United States Patent [19]

Stach

[11] Patent Number: 5,538,329
[45] Date of Patent: Jul. 23, 1996

[54] WHEEL FOR A MOTOR VEHICLE AND METHOD OF MAKING SAME

[75] Inventor: Jens Stach, Weil der Stadt, Germany

[73] Assignee: Dr. Ing. h.c.f. Porsche AG, Weissach, Germany

[21] Appl. No.: 262,100

[22] Filed: Jun. 16, 1994

Related U.S. Application Data

[63] Continuation of Ser. No. 8,852, Jan. 25, 1993, abandoned, which is a continuation-in-part of Ser. No. 979,274, Nov. 20, 1992, abandoned.

[30] Foreign Application Priority Data

Nov. 23, 1991 [DE] Germany .......................... 41 38 558.6
Jan. 24, 1992 [DE] Germany .......................... 42 01 838.2

[51] Int. Cl.$^6$ ...................................................... B60B 1/08
[52] U.S. Cl. ........................... 301/65; 301/64.1; 301/64.2; 301/104
[58] Field of Search ............................. 301/64.1, 65, 66, 301/67, 72, 73, 104, 64.2; 29/894.342

[56] References Cited

U.S. PATENT DOCUMENTS

| | | |
|---|---|---|
| 1,393,796 | 10/1921 | Lachman . |
| 1,602,512 | 10/1926 | Walther et al. . |
| 1,602,796 | 10/1926 | Jacobi et al. .......................... 301/64.2 |
| 1,610,023 | 12/1926 | Meldrum . |
| 1,613,127 | 1/1927 | Reyneri ............................... 301/64.2 |
| 1,635,490 | 7/1927 | Meldrum . |
| 1,850,345 | 3/1932 | Esksergian . |
| 1,952,474 | 3/1934 | Tarbox . |
| 2,107,950 | 2/1938 | Lejeune ............................... 301/64.1 |
| 3,862,779 | 1/1975 | Jayne . |
| 5,360,261 | 11/1994 | Archibald et al. ........................ 301/65 |

FOREIGN PATENT DOCUMENTS

| | | |
|---|---|---|
| 0004679 | 10/1979 | European Pat. Off. . |
| 447695 | 1/1913 | France . |
| 2347124 | 4/1977 | France . |
| 132949 | 1/1902 | Germany . |
| 2134485 | 2/1972 | Germany . |
| 2855308 | 7/1979 | Germany . |
| 4014368 | 3/1991 | Germany . |
| 29460 | of 1911 | United Kingdom . |
| 1351611 | 5/1974 | United Kingdom . |

OTHER PUBLICATIONS

Patent Abstracts of Japan, vol. 01, No. 7177 (M–1993), Apr. 6, 1993 & JP–A–04 334 601 (Mazda Motor Co.).

*Primary Examiner*—Russell D. Stormer
*Attorney, Agent, or Firm*—Evenson McKeown Edwards & Lenahan

[57] ABSTRACT

A rim for a motor vehicle has several radial hollow spokes in a wheel disk which is manufactured in a die tool and is connected with a rim well. The cast wheel disk is connected with a deformed rim well by friction welding in the area of a rim flange. On an interior side, the wheel disk has at least one flat welding surface which extends around as an annulus and which is arranged so that it corresponds with another opposite flat welding surface of the rim well. In at least one of the hollow spokes, one reinforcing rib is arranged which extends radially from the wheel center axis toward the outside and connects two opposite walls of the spoke with one another.

48 Claims, 7 Drawing Sheets

WHEEL FOR A MOTOR VEHICLE AND METHOD OF MAKING SAME

The present invention is a continuation of U.S. patent application Ser. No. 08/008,852, filed, which is a continuation-in-part of commonly assigned U.S. patent application Ser. No. 07/979,274, filed Nov. 20, 1992, both now abandoned.

BACKGROUND AND SUMMARY OF THE INVENTION

This invention relates to a wheel for a motor vehicle having a wheel disk portion which comprises several radial hollow spokes, is produced in a die tool and is connected with a rim well portion, a cast wheel disk portion being connected with a rim well comprising a deformed part via friction welding in the area of a ring flange. The wheel disk, on an interior side, has at least one flat welding surface which extends around as an annulus and corresponds with another opposite flat welding surface of the rim well.

In the case of wheels for motor vehicles made of cast metal, because of the fact that the wheel disk and the rim well are in one piece, a complicated sand core is required in the diecasting tool in order to be able to produce a wheel that is light in weight by means of a simple casting method. For those wheel rims with a direct connection to the wheel flange, accumulations of material are required in the area of the connection of the spokes to the rim well, and the casting of arbitrarily wide rim formats is limited. Also, the arrangement of the sand core parts between the cores of the diecasting tool for the formation of hollow spokes with constant wall thicknesses is possible only inadequately because of an insufficiently secured bearing of the core.

An object of the invention is to provide a wheel and a process for manufacturing the rim which in a simple manner can be manufactured in various dimensions and with a low weight.

It is another object of the invention to provide a wheel with a disk rim having hollow ribs that, while having a relatively small wall thickness, are constructed with high stability.

This and other objects are achieved by the present invention which provides a process for the manufacturing in a diecasting tool of an aluminum wheel with a cast wheel rim disk comprising a plurality of hollow spokes, the wheel disk being connected with a rim well consisting of a formed part. The wheel disk has an interior side with at least one plane welding surface which extends around the rim in a ring-shaped area, and the rim well has a corresponding plane welding surface. The process comprises arranging the plane welding surface of the wheel disk opposite the plane welding surface of the rim well, and connecting the wheel disk with the rim well by friction welding in an area of a rim flange of the aluminum rim.

The objects are also achieved by a wheel constructed according to the present invention which provides an aluminum wheel rim with a cast wheel wheel disk comprising a plurality of hollow spokes, the wheel rim disk being connected with a wheel rim well consisting of a formed part. The wheel rim disk has an interior side with at least one plane welding surface which extends around the wheel rim in a ring-shaped area, and the rim well has a corresponding plane welding surface, the plane welding surface of the wheel disk opposing the plane welding surface of the rim well. The wheel disk is connected with the rim well by friction welding in an area of a rim flange of the aluminum rim.

Some principal advantages achieved by means of the invention are that two separate constructional elements of the wheel can be connected with one another and therefore the casting operation for the wheel rim disk becomes possible by means of a sand core in the bottom core of the diecasting tool which is easy to support, and which, in addition must also be supported in a precise manner. The rim well can therefore be manufactured according to a different manufacturing technique, for example, by means of extruding or by hot-forming a blank so that a complicated diecasting tool is not required. Also, by using different manufacturing methods for the rim well and the rim disk, arbitrarily wide rim formats can be produced, and the rim well may then also consist of a different material than the wheel rim disk, which results in important advantages with respect to weight.

Because of the separation of the wheel rim disk from the rim well during the manufacturing of the two elements, a better castability of the wheel disk is achieved. In addition, a good supporting of the sand core becomes possible for the formation of hollow spokes with small and definitely uniformly thick wall thicknesses.

The two elements of the wheel, such as the wheel rim disk and the rim disk well are undetachably connected with one another by friction welding. For this purpose, the wheel rim disk has, on the interior side in the area of the rim space, two walls with face-side welding surfaces which are opposite corresponding welding surfaces on the rim well. Between the walls of both elements, a closed ring duct is formed which is connected with the space of the hollow spoke. As a result, the rim well forms a tight closure with respect to the fitted tire and a separate sealing of a space of the hollow spoke leading into the rim well.

According to the conditions, the welding surfaces on the faces of the walls of the two elements may be arranged either in a common plane or in different planes. This depends on the construction and is a function of the position of the hump on the rim well.

The supporting of the sand cores for the manufacturing of the rim, particularly in the area of the hollow spokes, is possible in different manners which takes place as a function of the construction of the hollow spokes. For example, the supporting of the sand cores takes place differently depending on whether these hollow spokes extend continuously directly to the hub; end at a distance from the hub; end in the fastening bores of the rims; or end in front of the fastening bores. In each of these cases, a sand core in the hollow spokes can be used for the forming of the hollow spokes which, because of its precise support, causes a uniformly relatively thin wall thickness of from 3.5 to 4 mm.

The aforementioned objects are also achieved by an embodiment of the present invention which provides a wheel with a cast wheel disk comprising a plurality of hollow spokes, the wheel disk being connected with a rim well that is a formed part. The wheel disk has an interior side with at least one plane welding surface which extends around the wheel in a ring-shaped area, and the rim well has a corresponding plane welding surface. The plane welding surface of the wheel disk is arranged opposite the plane welding surface of the rim well, and the wheel disk is connected with the rim well by friction welding in an area of a wheel flange of the aluminum rim. A hollow space is provided within at least one of the hollow spokes and has at least two opposite walls. A reinforcing rib is arranged in the hollow spoke to extend radially from a wheel center axis toward the outside of the wheel disk rim, wherein the reinforcing rib connects the two opposite walls with one another.

Some of the advantages achieved by the present invention are that the hollow ribs, while they have a relatively thin wall thickness, are reinforced by a rib situated in the interior. This reinforcing rib extends radially from the wheel hub approximately to the rim well and connects an exterior wall with an interior wall of the hollow space in the reinforcing rib. In the perpendicular direction, it is aligned in a vertical plane extending through the wheel spin axis and divides the rectangular hollow space into two chambers of approximately the same size. This hollow space has its largest width between two openings of the rim.

Other objects, advantages and novel features of the present invention will become apparent from the following detailed description of the invention when considered in conjunction with the accompanying drawings.

DETAILED DESCRIPTION OF THE DRAWINGS

Figure 1:
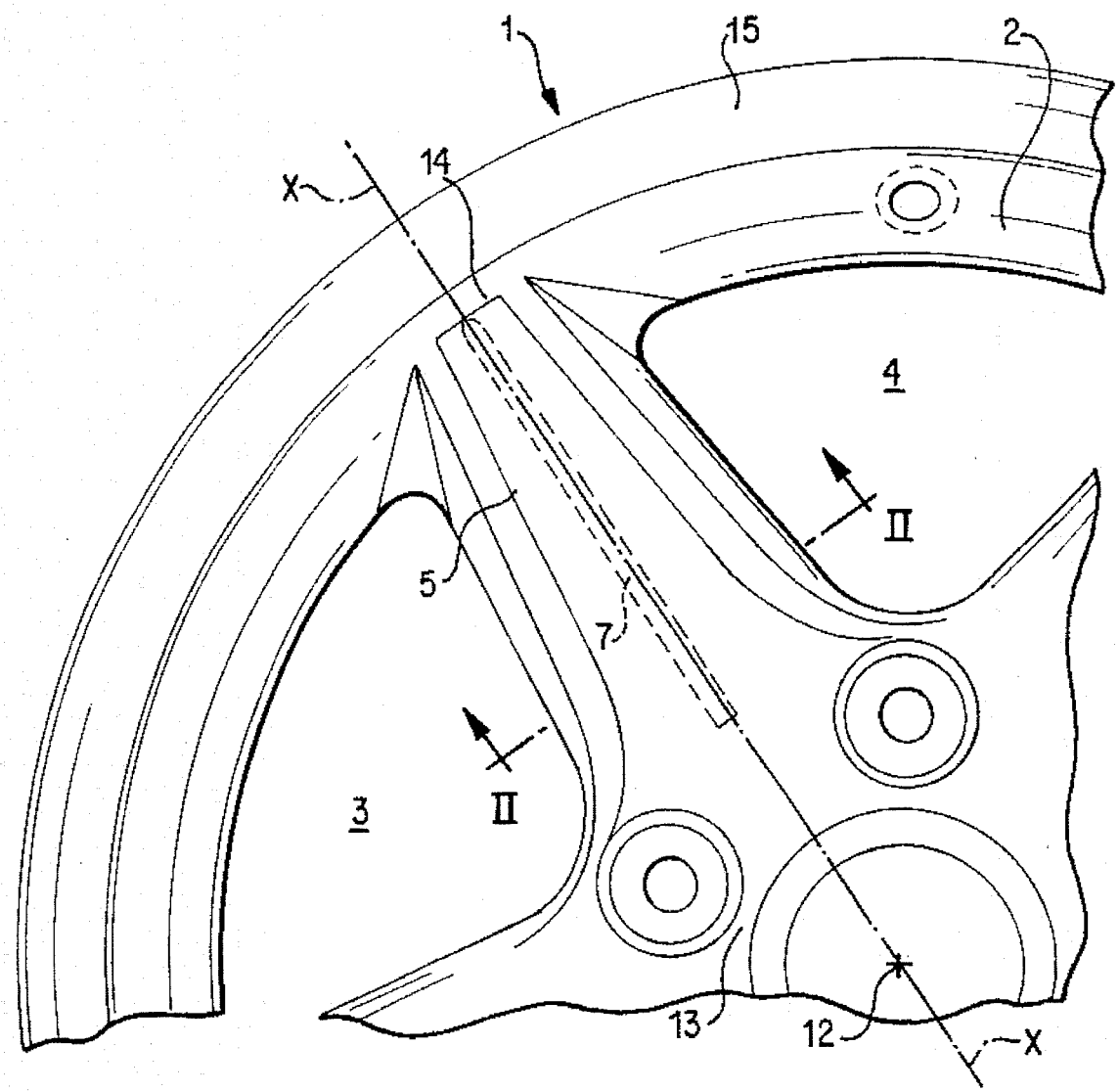
FIG. 1 is a frontal view of a partially shown rim.

The wheel 1 comprises two components—a rim disk 2 and a rim well. These two components are manufactured in various processes and are connected with one another, for example, by means of friction welding. The rim disk 2 is made of an aluminum alloy and is manufactured by die casting in a die tool. The rim disk 2 is cast in a die tool which comprises a lower core and an upper core. The rim well is made either from a cast blank by hot-forming on a roller press, or it may be made from an extruded tube section. The rim disk 2 is cast in a die tool which comprises a lower core and an upper core.

Radial hollow spokes 5 are arranged in the rim disk 2 between two air openings 3 and 4 respectively. The radial hollow spokes have a hollow space 6 exhibiting a rectangular cross-section with a center reinforcing rib 7. This hollow space 6 extends with a larger dimension (width b) in the plane Y—Y of the rim disk 2, with the smaller dimension (height a) arranged transversely with respect to plane Y—Y of the rim disk 2.

The reinforcing rib 7 divides the hollow space 6 into two equal cavities 8 and 9, and the rib 7 is connected with an exterior wall 10 and an interior wall 11. In particular, rib 7 with its height h extends in a perpendicular plane X—X extending through the wheel spin axis 12. The thickness d of the reinforcing rib 7 corresponds approximately to the exterior wall thickness d1.

The length of the reinforcing rib 7 is constructed according to the load to be absorbed. In the illustrated example according to FIG. 1, the rib 7 extends from the hub 13 to an outlet opening 14 on the edge 15 of the rim disk 2.

Figure 2:
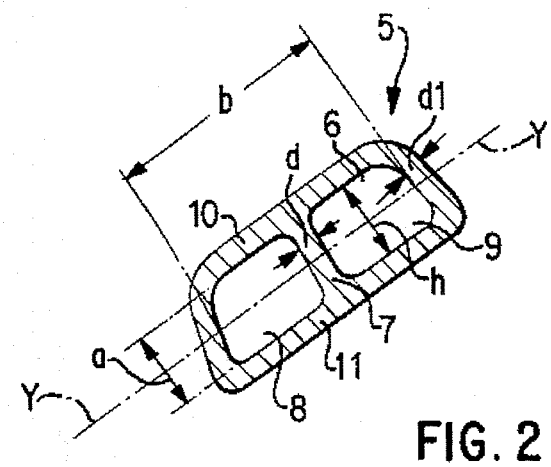
FIG. 2 is a sectional view according to Line II—II of FIG. 1.

The overall wheel construction will be explained with respect to FIGS. 3–10. As in FIGS. 1 and 2, the wheel 101 according to FIG. 3 essentially comprises two parts—a rim disk 102 and a rim well 103. These two parts are manufactured according to different processes and are connected with one another by friction weld R. The rim disk 102 may, for example, consist of an aluminum alloy and is manufactured by pressure diecasting in a diecasting tool. The rim well 103 is manufactured either from a cast blank by hot-forming on a roller pressure machine or may be made from an extruded pipe section.

Figure 6:
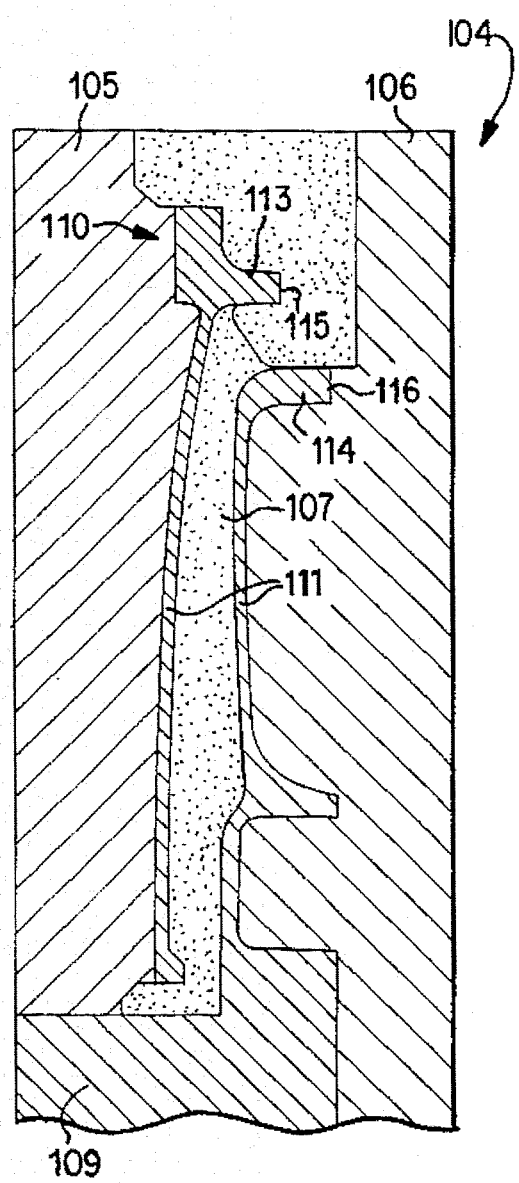
FIGS. 6 through 9 are views of different embodiments according to the present invention of sand cores in the diecasting tool for the formation of the hollow spokes.
Figure 7:
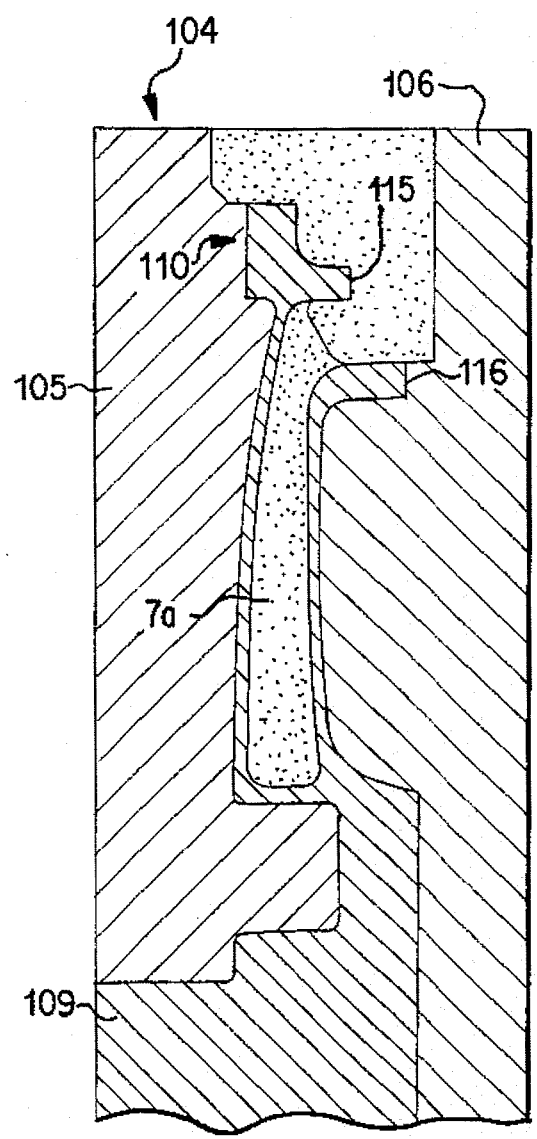
Figure 8:
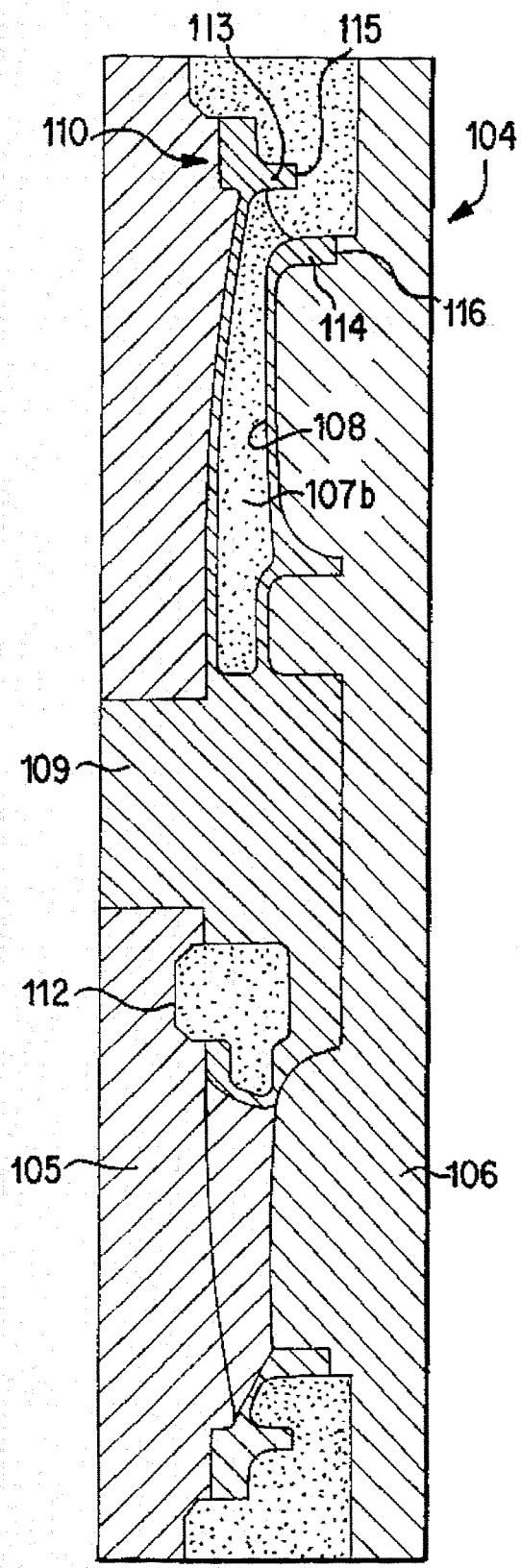
Figure 9:
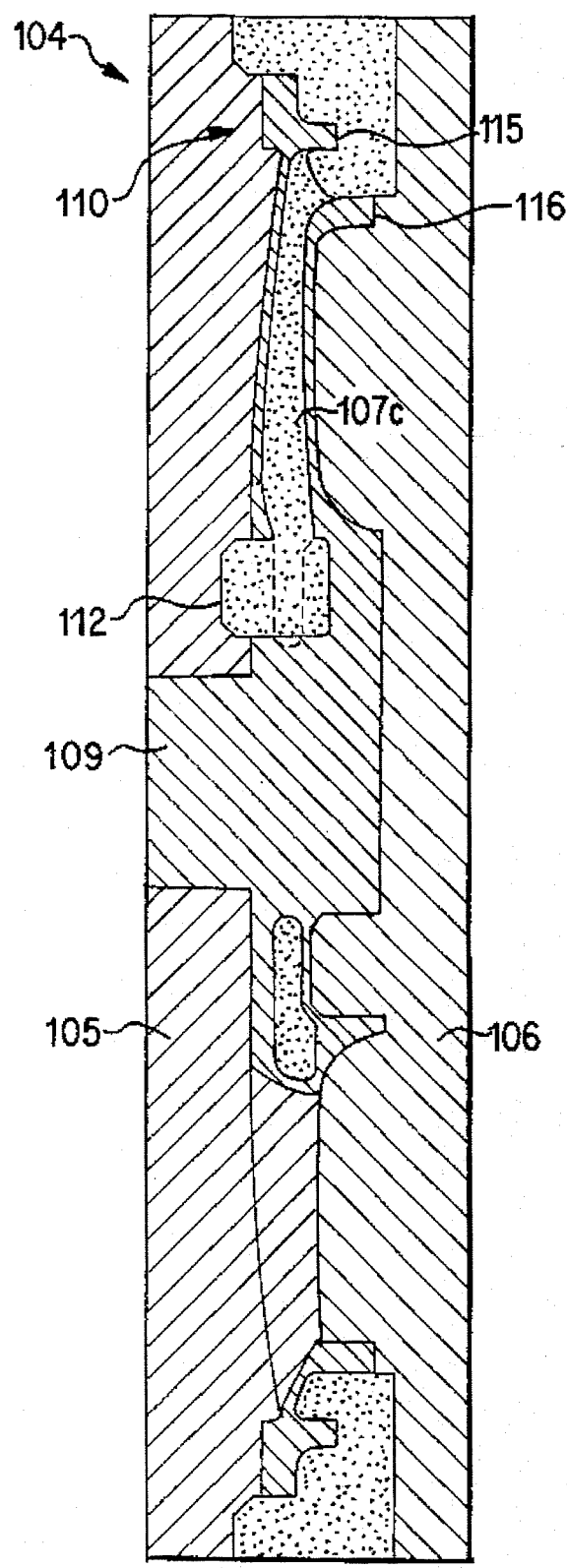

As shown in the examples of FIGS. 6 to 9, the rim disk 102 is cast in a diecasting tool 104 which has a bottom core 105 and top core 106. For achieving the wheel 101, a sand core 107 is arranged between cores 105 and 106. For the formation of the hollow spokes 108, this sand core 107 may be supported on the bottom core 105 in various manners. Thus, FIG. 6 shows the sand core 107 with a support in the area of the hub 109 as well as in the area of the rim flange 101. In the intermediate area of cores 105 and 106 and the sand core 107, the walls of the hollow spokes 108 are formed. In another embodiment according to FIG. 7, the sand core 107a is over-mounted, specifically in the area of the rim flange 110. Another bearing in the area of the hub 109 is not provided. Additional possibilities of the bearing of the sand core 107b and 107c are illustrated in FIGS. 8 and 9. In these embodiments, the sand core 107b and 107c is provided in the area of the rim flange 110 on the bottom core 105 as well as in the area of recesses 112 of fastening screws.

In the area of the rim flange 110, the sand core 107 to 107c is arranged in such a manner that walls 113 and 114 are formed on the rim disk 102 which are constructed as concentric ring-shaped areas, are situated in parallel and, on the face side, also form plane welding surfaces 115 and 116. These plane welding surfaces 115 and 116, corresponding with additional welding surfaces 115a and 116a, are disposed on walls 113a and 114a of the rim well 103.

These walls 113,114 and 113a, 114a form a partial space 117 and 118 between one another which, after the welded connection of the two rim parts 102 and 103, forms a closed annulus.

Figure 3:
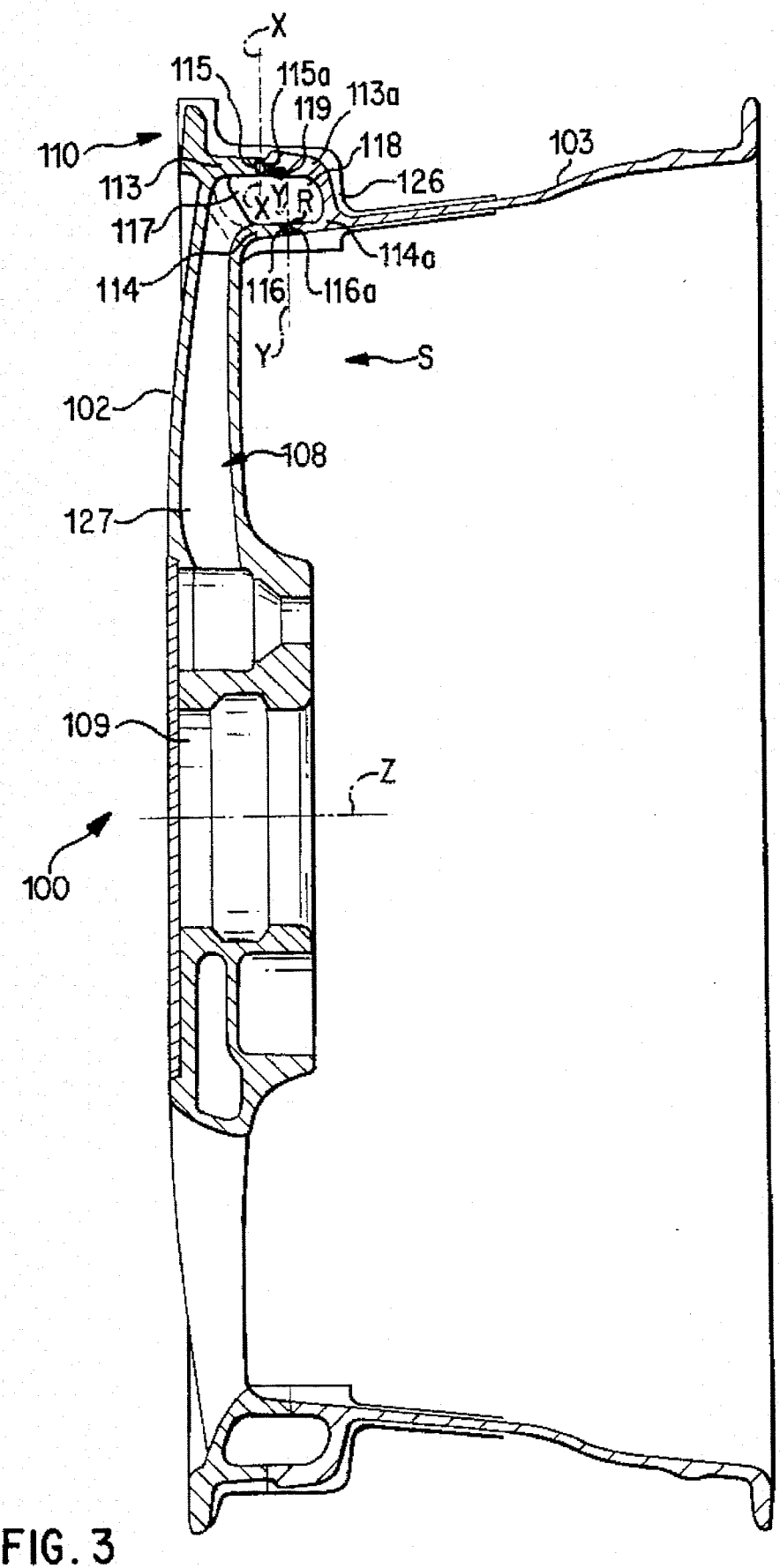
FIG. 3 is a sectional view of a rim through a hollow web constructed in accordance with an embodiment of the present invention.
Figure 4:
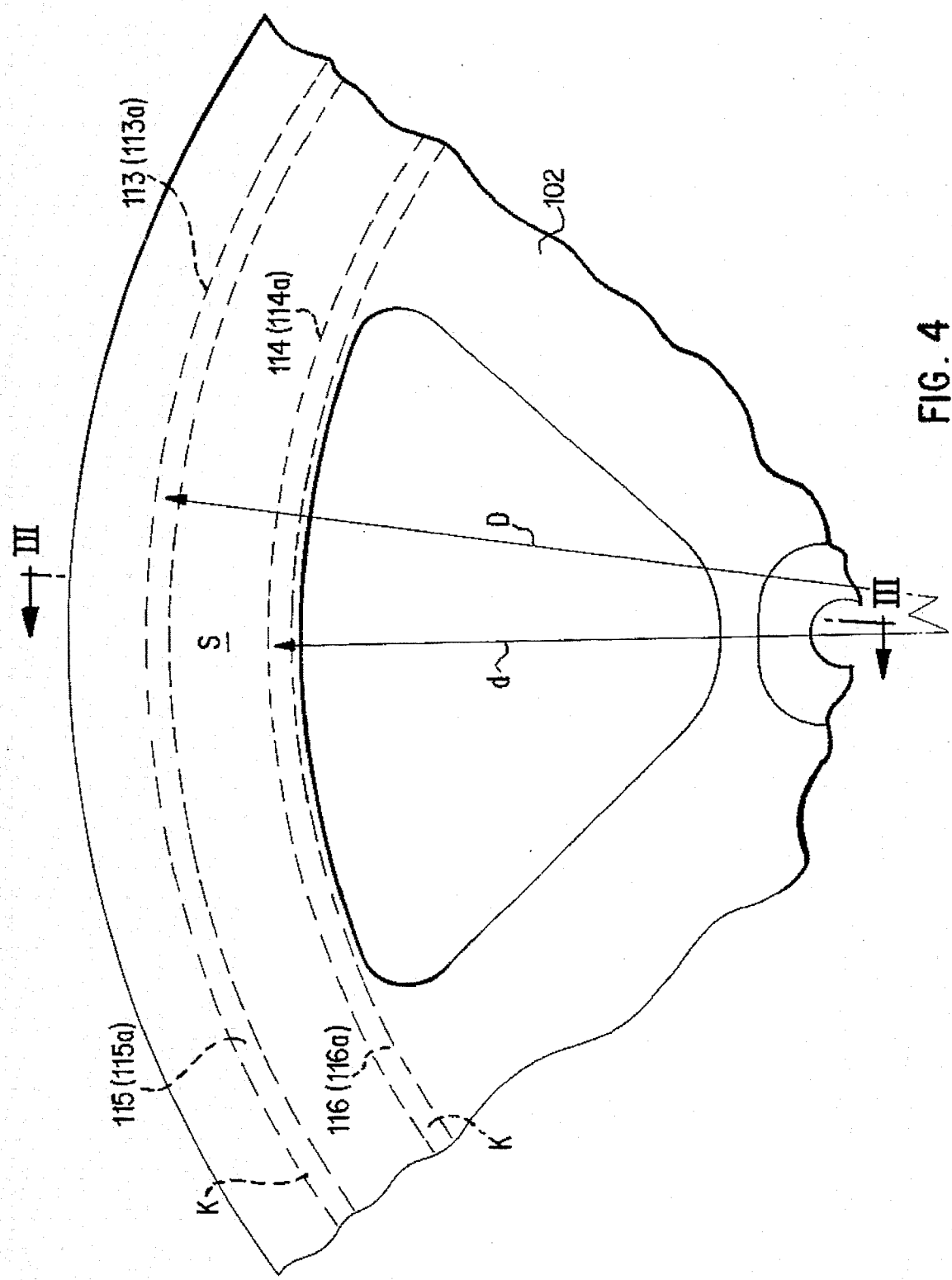
FIG. 4 is a partial section of the rim of FIG. 3 in the area of an air opening with welding surfaces.

As shown in FIG. 4, the walls 113 and 113a rest on a ring-shaped area of a larger diameter D than the diameter d on which the walls 114 and 114a rest. As shown in detail in FIG. 3, the welding surface 115 is, for example, arranged on the face of the wall 13 in a plane X—X which is set back with respect to the other welding surface 16 arranged in the plane Y—Y. Such a construction is necessary so that the hump 119 can still be completely assigned to the rim well 103. In the case of a different dimensioning of the rim well 103, the welding surfaces 115 and 116 may also be arranged in a common plane.

Figure 10:
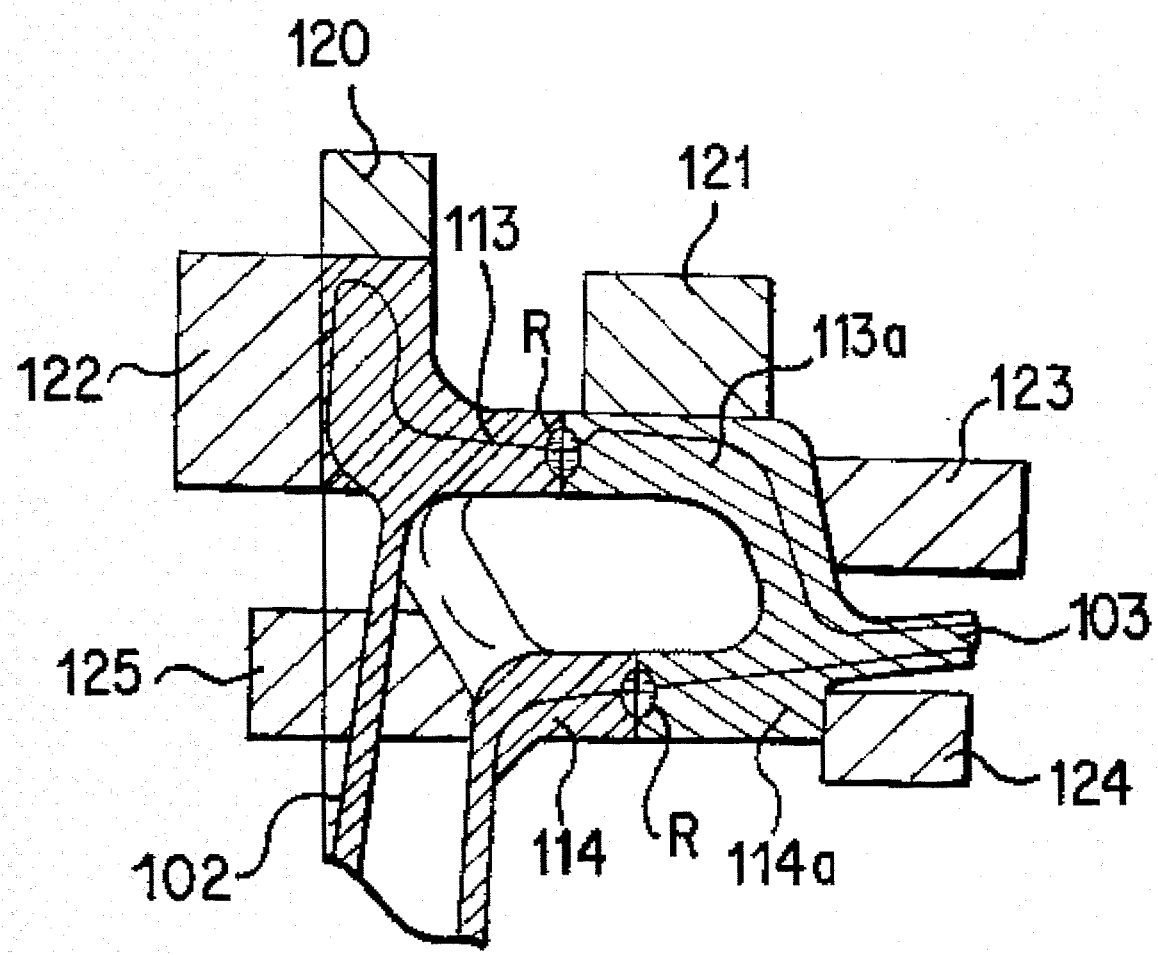
FIG. 10 is a view of an embodiment of the rim disk and the rim well for friction welding.

FIG. 10 illustrates in detail the arrangement of the wheel parts 102 and 103 for the friction welding R. In this manner, the wheel 101 is tensioned by devices 120,121 and is held by stops 122 to 125. In a known manner, a connection by means of friction welding R is obtained by the rotating of one of the rim parts 102 and 103.

The manufacturing of the rim well 103 from an extruded pipe section takes place in such a manner that, for the formation of the walls 113a and 114a with the pertaining face-side welding surfaces 15a and 16a, the pipe section is split on the face side and then the actual well of the rim 101 is completed by a machining bevel 126. A finishing of the surfaces of the rim well 103 takes place by turning to size.

The manufacturing of the rim well 103 from a cast blank takes place by hot-forming, in which case the well of the rim 101 is shaped by several rollers in a pressing machine to form a profiled rim well 103 with the walls 113*a* and 114*a* and the welding surfaces 115*a* and 116*a*.

Figure 5:
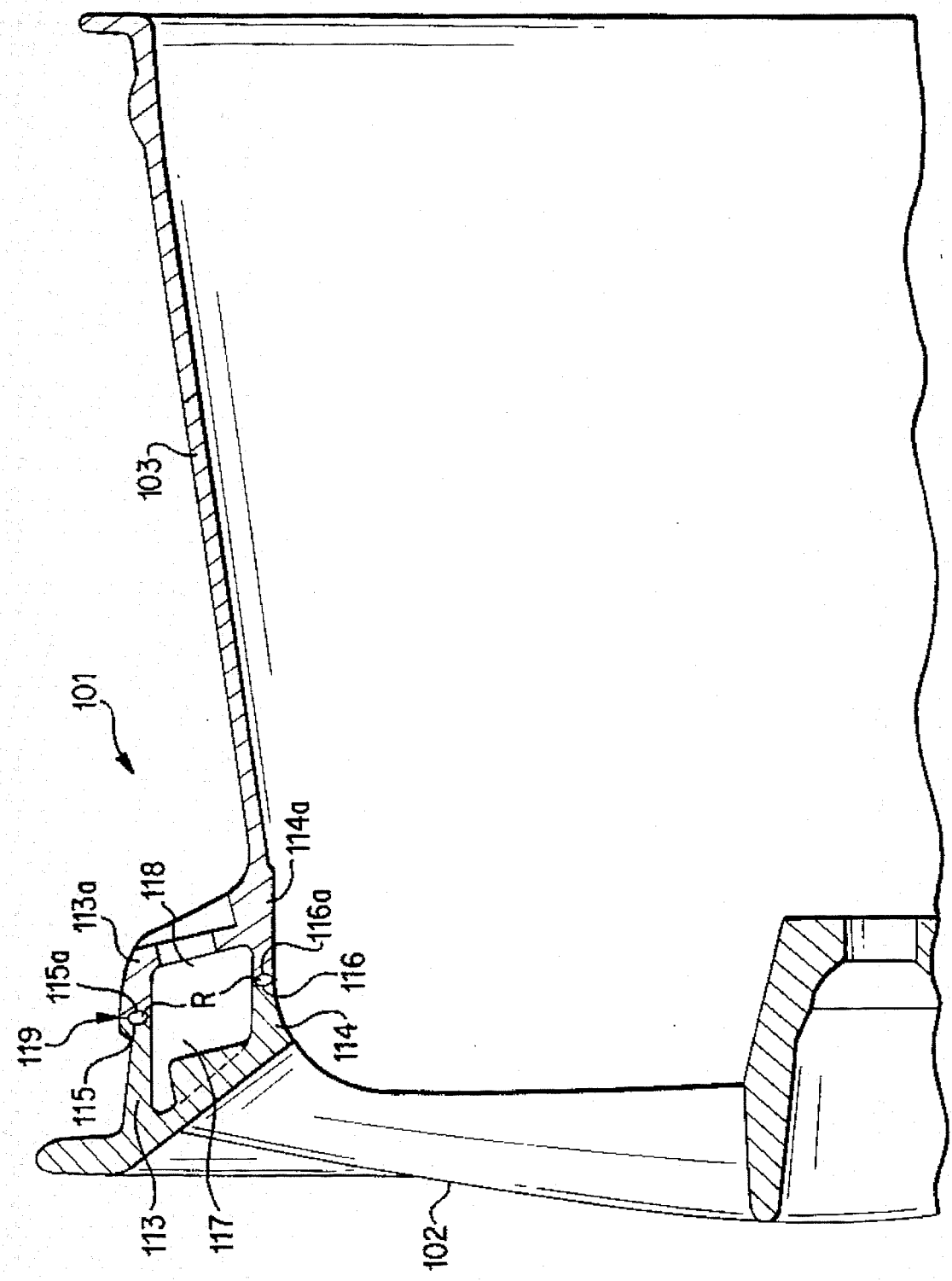
FIG. 5 is a sectional view according to Line III—III of FIG. 2 with welding surfaces.

As shown, for example, in FIGS. 3 and 5 in conjunction with FIG. 4, the hollow space 127 of the spoke 108 ends in the common annulus formed by the partial spaces 117 and 118, so that a separate sealing with respect to the tire is not necessary. Such a construction of the rim 101 is made possible essentially by the connection of rim parts 102 and 103 by friction welding R.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed:

1. A process for the manufacturing of an aluminum rim with a wheel disk comprising a plurality of hollow spokes in a diecasting tool, the wheel disk being connected with a rim well consisting of a formed part, the wheel disk having an interior side with at least one plane welding surface which extends around the rim in a ring-shaped area, and the rim well having a corresponding plane welding surface, the process comprising:

arranging the plane welding surface of the wheel disk opposite the plane welding surface of the rim well; and connecting the wheel disk with the rim well by friction welding in an area of a rim flange of the aluminum rim.

2. A process according to claim 1, wherein the rim well is formed from an extruded pipe section, and further comprising:

splitting the pipe section on a face side to form a gap and widening the gap to form the planar welding surfaces of the rim well;

performing a machining bevel on the pipe section; and pressure rolling the pipe section to complete forming of the rim well.

3. A process according to claim 1, wherein the rim well is a cast blank, and further comprising shaping the cast blank to a profiled rim well having face-side welding surfaces in walls via a plurality of rollers in a pressure machine.

4. A process according to claim 1, further comprising supporting a sand core on a bottom core of the diecasting tool in the area of the rim flange and of a hub, the sand core being arranged between these supports in an open manner with respect to the bottom core and a top core for formation of a uniform wall thickness of the hollow spokes.

5. A process according to claim 1, further comprising supporting a sand core in the area of the rim flange on a bottom core of the diecasting tool, and, by means of an end which faces away and is directed toward a hub, the sand core is arranged openly between the two cores for forming a uniform wall thickness of the hollow spokes.

6. A process according to claim 1, further comprising supporting a sand core in the area of the rim flange on a bottom core of the dicasting tool, said sand core being supported with its opposite end in recesses of the bottom core, with the area of the sand core situated between these supports arranged freely between the bottom core and the top core for formation of a uniform wall thickness of the hollow spokes.

7. An aluminum wheel comprising:

a diecast wheel disk having a plurality of hollow spokes and an interior side with at least one plane welding surface which extends around the rim in a ring-shaped area of a rim flange; and a formed rim well having a plane welding surface, the plane welding surface of the wheel disk opposing the plane welding surface of the rim well, wherein the wheel disk is connected to the rim well by a frictional weld at the plane welding surfaces of the wheel disk and the rim well at the ring-shaped area of the rim flange.

8. A rim according to claim 7, wherein a plurality of plane welding surfaces are provided on the faces of walls of the wheel disk, one wall with the welding surface having a diameter and being arranged directly in a first plane on the interior side of the rim flange, and the other plane welding surface on an opposite wall with a smaller diameter being provided in a second plane disposed in front on the interior side of the wheel disk, the plane welding surfaces being surrounding welding surfaces.

9. A rim according to claim 7, wherein the plane welding surfaces are opposingly arranged on faces of walls on the wheel disk and on the rim well in a common plane.

10. A rim according to claim 9, wherein between the walls which have the plane welding surfaces on the face side, open partial annuli which are in each case directed against one another, are formed on the wheel disk and on the rim well, the partial annuli forming a closed annulus which is connected with interior spaces of the hollow spokes, one exterior wall of the partial annulus having a hump and the other opposite interior wall forming a receiving surface for a compensating weight.

11. A rim according to claim 10, wherein the hump is in the exterior wall of the rim well which, together with the opposite interior wall, encloses the partial annulus.

12. A rim according to claim 7, wherein the hollow spokes of the wheel disk and sand cores which are removable through mouth openings of the hollow spokes, are formed between a lower and an upper core of a diecasting tool, the mouth openings as well as the plane welding surfaces being arranged at an approximately right angle with respect to the center rim axis.

13. A rim according to claim 7, wherein the rim disk and the rim well consist of different materials that are connected with one another by friction welding.

14. An aluminum wheel comprising:

a diecast wheel disk having plurality of hollow spokes and an interior side with at least one plane welding surface which extends around the rim in a ring-shaped area of a rim flange;

a formed rim well having a plane welding surface, the plane welding surface of the wheel disk opposing the plane welding surface of the rim well, wherein the wheel disk is connected to the rim well by a friction weld at the plane welding surfaces of the wheel disk and the rim well at the ring-shaped area of the rim flange;

a hollow space within at least one of the hollow spokes and having at least two opposite walls; and a reinforcing rib arranged in the hollow spokes to extend radially from a wheel center axis toward the outside of the wheel rim, wherein the reinforcing rib connects the two opposite walls with one another.

15. A rim according to claim 14, wherein the hollow space has an approximately rectangular cross-section, with a width in a rim plane of the hollow space that is larger than a depth of the cross-section.

16. A rim according to claim 15, wherein the opposite walls of the spokes include an interior wall and said exterior wall, and a reinforcing rib connecting the interior wall with the exterior wall.

17. A rim according to claim 16, wherein the rib extends along the whole length of the hollow spoke.

18. A rim according to claim 16, wherein the rib extends along the whole length of the hollow spoke.

19. A rim according to claim 15, wherein the rib extends along the whole length of the hollow spoke.

20. A rim according to claim 14, wherein the opposite walls of the spokes include an interior wall and said exterior wall, and a reinforcing rib connecting the interior wall with the exterior wall.

21. A rim according to claim 20, wherein the rib extends along the whole length of the hollow spoke.

22. A metal wheel comprising:
a wheel disk portion having a plurality of hollow spokes and an interior side with at least one plane welding surface which extends around the rim in a ring-shaped area of a rim flange;
a formed rim well portion having a plane welding surface, the plane welding surface of the wheel disk portion opposing the plane welding surface of the rim well portion, wherein the wheel disk portion is connected to the rim well portion by a friction weld at the plane welding surface of the wheel disk portion and the rim well portion at the ring-shaped area of the rim flange;
a hollow space within at least one of the hollow spokes and having at least two opposite walls; and
a reinforcing rib arranged in said at least one hollow spoke which connects the two opposite walls with one another.

23. A vehicle wheel comprising:
a wheel disk portion having a plurality of hollow spokes and at least one ring shaped friction welding surface,
and a rim well portion having a corresponding at least one ring shaped friction welding surface,
wherein said wheel disk portion and said rim well portion are connected by friction welding said at least one ring shaped friction welding surface to said corresponding at least one ring shaped friction welding surface.

24. A wheel according to claim 23, wherein the wheel disk portion and the rim well portion consist of different materials.

25. A wheel according to claim 24, wherein the hollow spokes have a wall thickness of between 3.5 mm and 4 mm.

26. A wheel according to claim 23, wherein the hollow spokes have a wall thickness of between 3.5 mm and 4 mm.

27. A wheel according to claim 26, wherein both the wheel disk portion and rim well portion are formed of aluminum.

28. A wheel according to claim 23, wherein said at least one ring shaped friction welding surface comprises a first and a second wall face of the wheel disk portion, said first wall face having a diameter and being arranged directly in a first plane on the interior side of a rim flange, and said second wall face having a smaller diameter and being provided in a second plane disposed on the interior side of the wheel disk portion, the first and second wall faces being circular welding surfaces.

29. A wheel according to claim 28, wherein said first plane and said second plane comprise a common plane.

30. A wheel according to claim 23, wherein said at least one ring shaped friction welding surface and said corresponding at least one ring shaped friction welding surface comprise open annuli which face each other, the open annuli forming a closed annulus which is connected with interior spaces of the hollow spokes when said wheel disk portion and said rim well portion are connected, an exterior wall of one of said open annuli having a hump and an opposite interior wall forming a receiving surface for a compensating weight.

31. A wheel according to claim 30, wherein the hump is in an exterior wall of the rim well portion.

32. A wheel according to claim 23, wherein the hollow spokes of the wheel disk portion and sand cores which are removable through mouth openings of the hollow spokes, are formed between a lower and an upper core of a diecasting tool, the mouth openings as well as the welding surfaces being arranged at an approximately right angle with respect to a center wheel axis.

33. A wheel according to claim 23, wherein both the wheel disk portion and rim well portion are formed of aluminum.

34. A vehicle wheel comprising:
a wheel disk portion having a plurality of hollow spokes and a pair of concentric ring shaped friction welding surfaces,
and a rim well portion having a corresponding pair of concentric ring shaped friction welding surfaces,
wherein said wheel disk portion and said rim well portion are connected by friction welding said pair of concentric ring shaped friction welding surfaces to said corresponding pair of concentric ring shaped friction welding surfaces.

35. A wheel according to claim 34, wherein the hollow spokes have a wall thickness of between 3.5 mm and 4 mm.

36. A wheel according to claim 34, wherein both the wheel disk portion and rim well portion are formed of aluminum.

37. A vehicle wheel comprising:
a wheel disk portion having a plurality of hollow spokes and at least one ring shaped friction welding surface,
and a rim well portion having a corresponding at least one ring shaped friction welding surface,
wherein said wheel disk portion and said rim well portion are connected by friction welding said at least one ring shaped friction welding surface to said corresponding at least one ring shaped friction welding surface, and
wherein each of said hollow spokes is provided with a reinforcing rib extending radially with respect to a wheel disk hub portion.

38. A wheel according to claim 37, wherein both the wheel disk portion and rim well portion are formed of aluminum.

39. A process for the manufacturing of a vehicle wheel, with a wheel disk portion having a plurality of hollow spokes connected with a rim well portion, the wheel disk portion having an interior side with at least one plane welding surface which extends annularly around a center axis in a ring-shaped area, and the rim well portion having a corresponding at least one plane welding surface, the process comprising:
arranging the at least one plane welding surface of the wheel disk portion opposite the at least one plane welding surface of the rim well portion; and
connecting the wheel disk portion with the rim well portion by friction welding along the respective plane welding surfaces.

40. A process according to claim 39, wherein the rim well portion is formed from an extruded pipe section, and further comprising:

splitting the pipe section on a face side to form a gap and widening the gap to form the at least one planar welding surfaces of the rim well portion;

performing a machining bevel on the pipe section; and pressure rolling the pipe section to complete forming of the rim well portion.

41. A process according to claim 39, wherein the rim well portion is a die cast blank, and further comprising shaping the cast blank to a profiled rim well portion having said at least one welding surface via a plurality of rollers in a pressure machine.

42. A process according to claim 39, further comprising supporting a sand core on a bottom core of a diecasting tool in the area of a rim flange and of a hub, the sand core being arranged between these supports in an open manner with respect to the bottom core and a top core for formation of a uniform wall thickness of the hollow spokes of the wheel disk portion.

43. A process according to claim 39, further comprising supporting a sand core in an area of a wheel disk portion rim flange on a bottom core of a diecasting tool, and, by means of an end which faces away and is directed toward a wheel hub portion of the wheel disk portion, the sand core is arranged openly between the two cores for forming a uniform wall thickness of the hollow spokes.

44. A process according to claim 39, further comprising supporting a sand core in an area of a wheel disk portion rim flange on a bottom core of a diecasting tool, said sand core being supported with its opposite end in recesses of the bottom core, with the area of the sand core situated between these supports arranged freely between the bottom core and the top core for formation of a uniform wall thickness of the hollow spokes.

45. A method of manufacturing a vehicle wheel comprising:

providing a wheel disk portion having a plurality of hollow spokes and at least one ring shaped friction welding surface, providing a rim well portion having a corresponding at least one ring shaped friction welding surface, and connecting said wheel disk portion and said rim well portion by friction welding said at least one ring shaped friction welding surface to said corresponding at least one ring shaped friction welding surface.

46. A method according to claim 45, wherein the wheel disk portion and the rim well portion consist of different materials.

47. A method of manufacturing a vehicle wheel comprising:

providing a wheel disk portion having a plurality of hollow spokes and a pair of concentric ring shaped friction welding surfaces, providing a rim well portion having a corresponding pair of concentric ring shaped friction welding surfaces, and connecting said wheel disk portion and said rim well portion by friction welding said pair of concentric ring shaped friction welding surfaces to said corresponding pair of concentric ring shamed friction welding surfaces.

48. A method of manufacturing a vehicle wheel comprising:

providing a wheel disk portion having a plurality of hollow spokes and at least one ring shaped friction welding surface, providing a rim well portion having a corresponding at least one ring shaped friction welding surface, and connecting said wheel disk portion and said rim well portion by friction welding said at least one ring shaped friction welding surface to said corresponding at least one ring shaped friction welding surface, wherein each of said hollow spokes is provided with a reinforcing rib extending radially with respect to a wheel disk hub portion.

* * * * *